United States Patent [19]

Geiss

[11] 4,230,109
[45] Oct. 28, 1980

[54] APPARATUS FOR SECURING COUPLINGS OF INTRAVENOUS AND INTRA-ARTERIAL ACCESS SYSTEMS

[76] Inventor: Alan Geiss, 50 Brampton La., Great Neck, N.Y. 11030

[21] Appl. No.: 935,669

[22] Filed: Aug. 21, 1978

[51] Int. Cl.³ .............................................. A61M 5/00
[52] U.S. Cl. ................................ 128/214 R; 128/247; 285/114
[58] Field of Search ................ 128/214 R, 214.2, 247, 128/DIG. 26, 334 C, 348; 285/114

[56] References Cited

U.S. PATENT DOCUMENTS

| 3,167,072 | 1/1965 | Stone et al. ...................... 128/214 R |
| 3,489,146 | 1/1970 | Rubin et al. ...................... 128/214 R |
| 3,881,753 | 5/1975 | Bochory ............................ 285/114 X |
| 4,082,094 | 4/1978 | Dailey ............................... 128/214 R |

FOREIGN PATENT DOCUMENTS 1506163  4/1978  United Kingdom ................ 128/214 R Primary Examiner—Dalton L. Truluck

[57] ABSTRACT

An apparatus for preventing separation of coupled fluid conduits in a vascular access system. In one embodiment first and second means are provided for affixing to respective ones of coupled fluid conduits. In a second embodiment first and second means are provided for abutting surfaces of connectors forming a part of and joining the fluid conduits, each surface facing away from the other fluid conduit. In both embodiments, the first and second means are joined such that motion of the first conduit from coupled relation with the second conduit is restrained.

10 Claims, 8 Drawing Figures ary access device, the
venous catheter includes a thin, flexible tube which is
insertible into the vein and a connecting hub axially
aligned with the tube for coupling a section of tubing, a
fluid valve or other device to the catheter for the purpose of infusing a liquid in or removing blood from the
patient's vein. The catheter hub is provided with an
axial opening to receive a male connector of the tubing,
valve or other device to be coupled to the catheter.
After the catheter has been inserted into the patient's
vein, the male connector is forced into the axial opening
of the catheter hub and is retained therein by friction of
that surface portion of the male connector which is in
contact with a receptacle of the catheter hub.

The tubing or other device attached directly to the
male connector normally is held to the patient's skin by
one or more pieces of tape wrapped around or over the
tubing or other device and placed against the skin to
form an adhesive bond therewith. However, the area of
the skin in contact with the tape frequently becomes
wet and the tape is then prone to lose its ability to adhere to the skin. Catheter tubing can get caught on the
patient's clothing, bed or other objects and is, thus,
frequently subject to forces which tear the tape holding
the male connector from the patient's skin and the male
connector from the hub of the catheter. Often patients
are confused and pull at the catheter tubing, causing the
male connector to separate from the hub of the catheter.
Separation of the various fluid conduits of an intravenous catheter system is, accordingly, a fairly common
occurrence, and in all such cases, the danger of serious
injury or death of the patient as a consequence of air
embolism is present.

As in the case of the intravenous system, intra-arterial
catheters are each provided with a hub for coupling to
a male connector attached to a tube, valve or other
element of the intra-arterial fluid access system; the
intra-arterial catheter hub holds the male connector in
the same manner, i.e. by friction. Accordingly, the same
circumstances giving rise to a disconnection of the intravenous catheter hub from the male connector can
exist for the intra-arterial system. Such a disconnection
can result in massive hemorrhage through the opening
of the hub with substantial likelihood that the patient
will die as a consequence.

SUMMARY OF THE INVENTION

The present invention provides an apparatus preventing separation of coupled fluid conduits in a vascular
access system. This is accomplished in one illustrative
embodiment of the present invention by the provision of
a first means for abutting a surface of a first one of a pair
of connectors coupling the fluid conduits, the surface of
the first connector facing away from a second one of the
connectors; and a second means for abutting a surface of
the second connector, the surface of the second connector facing away from the first connector. The second
means is joined with the first means such that motion of
the first connector from coupled relation with the second connector is restrained.

In a second embodiment of the present invention,
there is provided a first means for affixing to a first one
of the coupled fluid conduits, and a second means for
affixing to a second one of the coupled fluid conduits.
The second means is joined with the first means such
that motion of the first fluid conduit from coupled relation with the second fluid conduit is restrained.

BRIEF DESCRIPTION OF THE DRAWINGS

The present invention, as well as further features
thereof, will be understood more clearly and fully from
the following description of certain preferred embodiments, when read with reference to the accompanying
drawings, in which.

DESCRIPTION OF CERTAIN PREFERRED EMBODIMENTS

Figure 1:
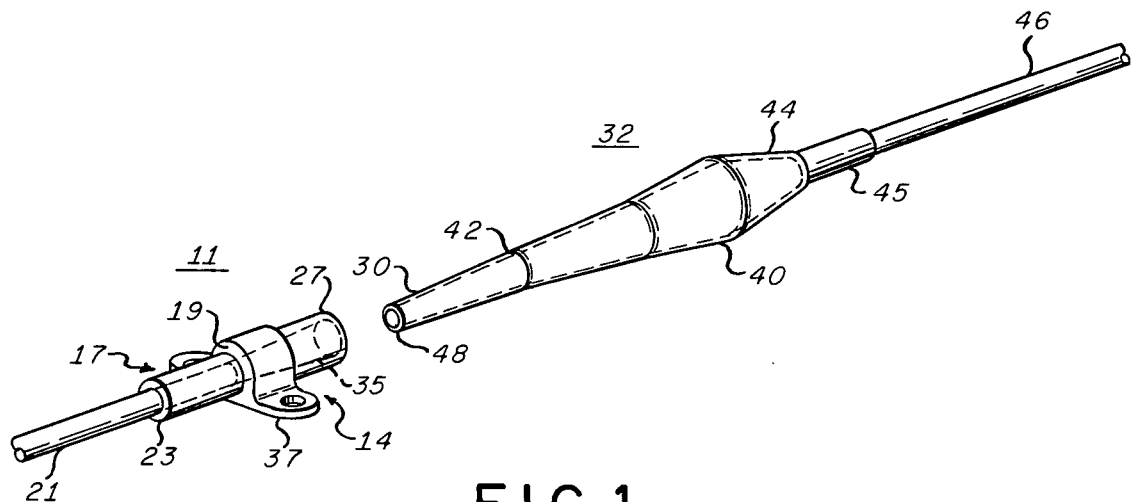
FIG. 1 is a diagramatic view of a catheter hub and a
male connector therefor, aligned axially for coupling
together.

With reference to FIG. 1, a pair of conventional
connectors used for coupling fluid conduits in intravenous and intra-arterial access systems is shown. A hub
11 of the type used especially for coupling catheters to
other fluid conduits such as valves, filters and the like,
includes a generally cylindrical body 14 and a cylindrical projection 17 axially aligned with body 14. Projection 17 has a smaller diameter than body 14 and has one
end joined thereto such that an annular end surface 19
of body 14 faces toward projection 17. Projection 17 is
axially aligned with a catheter tube 21 joined thereto at
an end surface 23 of projection 17 in opposed parallel
relation with said one end of projection 17.

A receptacle 27 of body 14 is formed at an end
thereof opposite annular surface 19 and is adapted to
receive and retain a projection 30 of a male connector 32. Receptacle 27 has an inner surface 35, shown in phantom lines, defining a conical cavity coaxial with body 14. Said cavity of receptacle 27 is accessible through an axial opening in the end of body 14 opposite annular end surface 19, the axial opening being defined by a lip 38 of receptacle 27. Receptacle 27 has a hollow interior communicating with the cavity of receptacle 27 and with catheter tube 21 to permit the passage of fluids from said cavity to tube 21. Two flanges 37 project from the sides of body 14 to provide a means through which a suture may be passed to affix the hub to the patient's skin to prevent removal of the catheter tube from a vein or artery.

Male connector 32 also includes a flexible bulb 40 of generally conical shape coaxial with projection 30 and having a first end joined thereto at a first end 42 of projection 30. A second end 44 of bulb 40 is coaxially joined with a cylindrical tube connector 45 which is connected with further components such as a filter, valve or the like, through a tube 46 to receive or transmit a fluid to or from such components. Projection 30 is conically shaped and has a second end 48 having a smaller diameter than first end 42. Projection 30 has a hollow interior accessible through openings in first end 42 and second end 48. Bulb 40 has a hollow interior communicating with the hollow interior of projection 30 through the opening in first end 42 and with the tube connector 45 through an opening in second end 44 of bulb 40. When inserted in receptacle 27, projection 30 communicates with hub 11 to conduct fluids to or from tube 46 through bulb 44 to or from catheter tube 21. Bulb 44 provides a means for applying a slight positive pressure to the fluid to clear a blockage in the fluid flow path.

Projection 30 is held in receptacle 27 through friction between projection 30 and the inner surface 35 of receptacle 27. The frictional bond thus formed is easily broken by a relatively small axial force. As mentioned above, taping tube 46 to the patient's skin does not insure against this occurance since the tape tends to come loose from the skin when wet. Even if the tape does not break away from the skin, projection 30 can separate from receptacle 27 since the skin is flexible, permitting male connector 32 to pull away from hub 11 upon the application of an axial force to male connector 32. Moreover, a force applied to the skin causing it to stretch, can exert a force on male connector 32 through the tape urging it away from hub 11. When the hub coupling a catheter tube inserted within a vein or artery separates from a connector joining the catheter and hub to the remainder of the fluid system, the vein or artery is opened to the air raising the possibility of air embolism or massive hemorrhage, which can in turn lead to serious injury and death.

Figure 2:
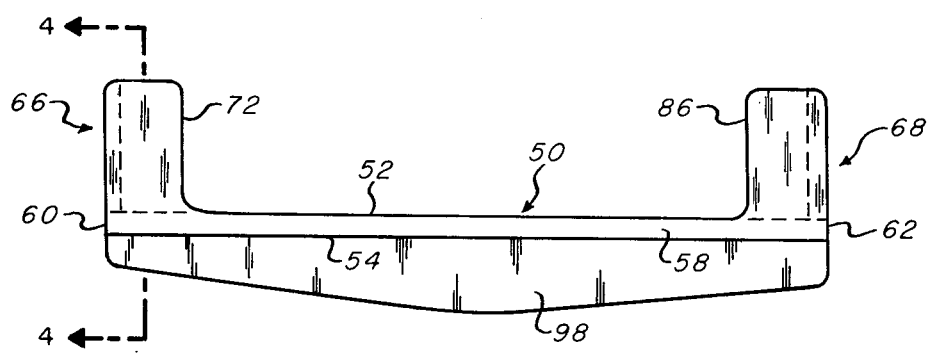
FIG. 2 is a diagramatic elevational view of a device in
accordance with one illustrative embodiment of the
present invention.
Figure 3:
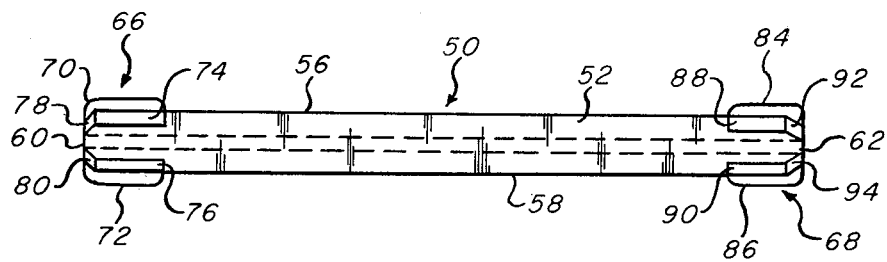
FIG. 3 is a view looking down on the device of FIG. 2.
Figure 4:
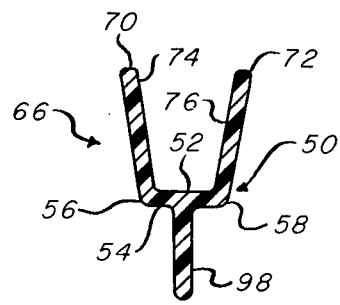
FIG. 4 is a sectional view taken along line 4—4 in FIG. 2.

The illustrated embodiments of the invention provide a secure coupling able to resist normal axial forces applied to the components of the system. With reference to FIGS. 2, 3 and 4, a device adapted for retaining the male connector 32 of FIG. 1 securely in receptacle 27 of hub 11, is shown. Corresponding elements shown in FIGS. 2, 3 and 4 are designated by the same reference numerals. A platform 50 has a generally rectangular top surface 52 and a generally rectangular bottom surface 54 in opposed parallel relation with and spaced from top surface 52. A first side 56 of platform 50 joins a first long edge of top surface 52 with a first long edge of bottom surface 54. A second side 58 of platform 50 in opposed parallel relation with first side 56, joins a second long edge of top surface 52 with a second long edge of bottom surface 54. A first end 60 of platform 50 joins a first short edge of top surface 52 with a first short edge of bottom surface 54. A second end 62 of platform 50 in opposed parallel relation with first end 60 joins a second short edge of top surface 52 with a second short edge of bottom surface 54.

Two clips 66 and 68 are affixed to the top surface 52 of platform 50 adjacent respective ends 60 and 62 thereof. Clip 66 has a first projecting member 70 extending from a portion of top surface 52 adjacent first end 60 and first side 56, and a second projecting member 72 extending from a portion of top surface 52 adjacent first end 60 and second side 58. A flat inner surface 74 of first projecting member 70 faces toward a flat inner surface 76 of second projecting member 72. Inner surfaces 74 and 76 are angled slightly away from the normal of top surface 52 such that inner surfaces 74 and 76 are spaced closest adjacent top surface 52 and face slightly away therefrom, as shown in FIG. 4.

Clip 66 further includes a pair of opposed tapered ribs 78 and 80 each joined to a respective one of inner surfaces 74 and 76 of projecting members 70 and 72. Tapered ribs 78 and 80 extend from top surface 52 of platform 50 adjacent first end 60 thereof and are coextensive with inner surfaces 74 and 76, respectively. Each of ribs 78 and 80 has a wide base where it joins the corresponding one of inner surfaces 74 and 76 and a ridge in parallel opposed relation with its base.

Clip 68 has a first projecting member 84 extending from a portion of top surface 52 adjacent second end 62 and first side 56, and a second projecting member 86 extending from a portion of top surface 52 adjacent second end 62 and second side 58. Projecting member 84 has a flat inner surface 88 facing toward a flat inner surface 90 of projecting member 86. As in the case of inner surfaces 74 and 76, inner surfaces 88 and 90 are angled slightly away from the normal of top surface 52 such that they are spaced closest adjacent top surface 52 and face slightly away therefrom.

Clip 68 is provided with a pair of opposed tapered ribs 92 and 94 similar to ribs 78 and 80 of clip 66. Each of ribs 92 and 94 is joined to a respective one of inner surfaces 88 and 90 and extend from top surface 52 of platform 50 adjacent second end 62 thereof. Ribs 92 and 94 are coextensive with inner surfaces 88 and 90, respectively. Each of ribs 92 and 94 has a wide base where it joins the corresponding one of inner surfaces 88 and 90 and a ridge in parallel opposed relation with its base.

Clips 66 and 68 and platform 50 preferably are made of hard, molded plastic in an integral construction. However, the plastic chosen should have sufficient flexibility to permit a catheter hub, male connector, tube or the like to be wedged between the projecting members of clips 66 and 68 and retained thereby.

A reinforcing web 98 projects from a portion of bottom surface 54 of platform 50 equidistant from sides 56 and 58 and extending from first end 60 to second end 62. Web 98 has a width parallel with bottom surface 54 approximately equal to the distance separating top surface 52 of platform 50 from bottom surface 54, and has a generally V-shaped elevational contour such that the elevational dimension of web 98 is a minimum at ends 60 and 62 of platform 50 and a maximum halfway between ends 60 and 62. Web 98 is preferably formed of hard plastic integrally with platform 50 and clips 66 and 68. Platform 50 and web 98 provide a means for supporting clips 66 and 68 in fixed relation such that catheter hubs, tubes, connectors and the like in coupled relation and retained by clips 66 and 68 will be prevented from separating.

Figure 5:
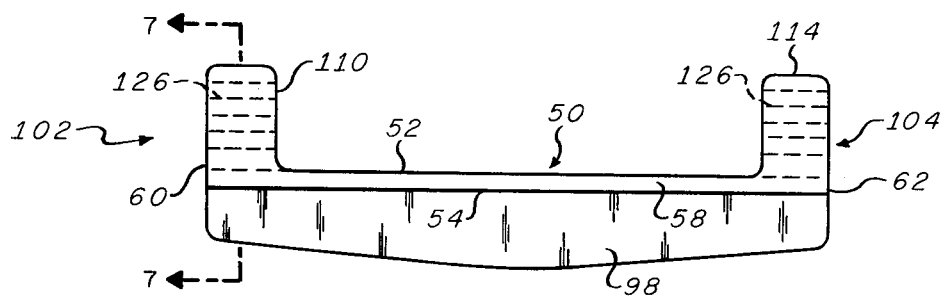
FIG. 5 is a diagramatic elevational view of a device in
accordance with another illustrative embodiment of the
present invention.
Figure 6:
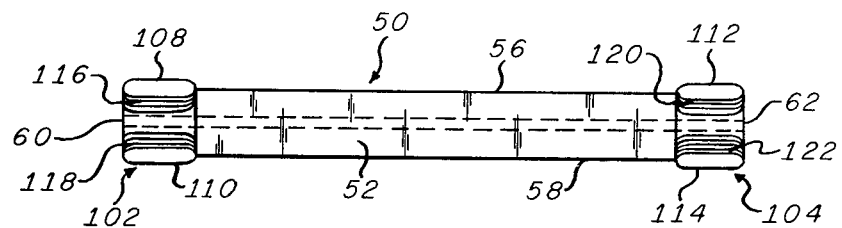
FIG. 6 is a view looking down on the device in FIG. 5.
Figure 7:
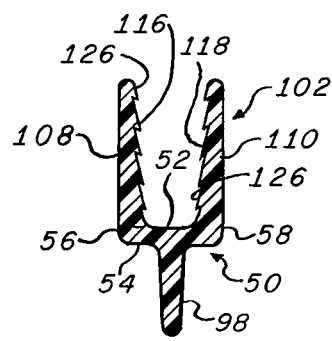
FIG. 7 is a sectional view taken along line 7—7 of FIG. 5.

With reference to FIGS. 5, 6 and 7, a device in accordance with another illustrative embodiment of the invention is shown. The device of FIGS. 5, 6 and 7 includes a platform 50 and a reinforcing web 98 corresponding in size and shape to platform 50 and web 98 of FIGS. 2, 3 and 4 and related in the same manner. The device of FIGS. 5, 6 and 7 further includes a first clip 102 disposed on top surface 52 of platform 50 adjacent first end 60 thereof and a second clip 104 disposed on top surface 52 adjacent second end 62 thereof. First clip 102 includes a first projecting member 108 extending from a portion of surface 52 adjacent first end 60 and first side 56 of platform 50 and a second projecting member 110 extending from a portion of surface 52 adjacent first end 60 and second side 58 of platform 50. Second clip 104 includes a first projecting member 112 extending from a portion of surface 52 adjacent second end 62 and first side 56 and a second projecting member 114 extending from a portion of surface 52 adjacent second end 62 and second side 58.

With particular reference to FIG. 7, first projecting member 108 of clip 102 has an inner surface 116 facing toward an inner surface 118 of second projecting member 110. First projecting member 112 of clip 104 has an inner surface 120 facing toward an inner surface 122 of second projecting member 114. Inner surfaces 116, 118, 120 and 122 are each angled and face slightly away from the normal of top surface 52 such that they are spaced closest adjacent top surface 52. Each of surfaces 116, 118, 120 and 122 is provided with a plurality of tapered ribs 126 arranged in parallel spaced relation to each other and surface 52, so that each of the ribs 126 on surfaces 116 and 120 is directly opposite a corresponding one of the ribs 126 on an opposing one of surfaces 118 and 120, said corresponding ribs being equally spaced from surface 52.

As in the case of the device shown in FIGS. 2, 3 and 4, the device of FIGS. 5, 6 and 7 is preferably made of hard, molded plastic in an integral construction, the plastic having sufficient flexibility such that a catheter hub, male connector, tube or the like may be wedged between the projecting members of clips 102 and 104. Ribs 126 of clips 102 and 104 are spaced appropriately to close over the object wedged therein and retain it in such position. It will be appreciated that, through the provision of multiple rib pairs on the inner surfaces of members 108, 110, 112 and 114, objects of various sizes may be retained therein.

Figure 8:
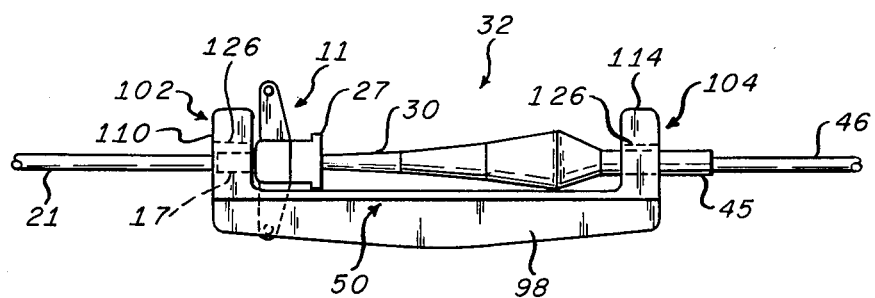
FIG. 8 is a diagramatic view of the device of FIGS. 5, 6 and 7 arranged to secure the hub and male connector of FIG. 1 in coupled relation.

FIG. 8 illustrates how the device of FIGS. 5, 6 and 7 is employed to secure the catheter hub 11 and male connector 32 of FIG. 1 in coupled relation. First, projection 30 of connector 32 is inserted in receptacle 27 of hub 11. Then cylindrical projection 17 is wedged between members 108 and 110 of clip 102 past a pair of corresponding ribs 126 thereof, which then close over cylindrical projection 17 to retain it therein. Simultaneously, tube connector 45 of male connector 32 is wedged between members 112 and 114 of clip 104 past a pair of corresponding ribs 126 of members 112 and 114 which retain tube connector 45 in the same manner as cylindrical projection 17 is retained by the ribs of clip 102, such that hub 11 and connector 32 are coupled together and to clips 102 and 104 as shown in FIG. 8.

By virtue of the fact that clips 102 and 104 are joined to platform 50 as part of a rigid structure, the former are held in a rigid spaced relation. Hub 11 and connector 32 are held frictionally by clips 102 and 104. However, upon the application of an axial force tending to separate hub 11 and connector 32 and sufficient to break the frictional hold of clips 102 and 104, separation of hub 11 from connector 32 will be prevented since surface 19 of hub 11 will abut members 108 and 110 of clip 102 and bulb 40 of connector 32 will abut members 112 and 114 of clip 104. In like manner, the device of FIGS. 2, 3 and 4 is adapted to hold cylindrical projection 17 and tube connector frictionally against tapered ribs 78, 80, 92 and 94 of clips 66 and 68. In the event that a force applied to hub 11 and connector 32 is sufficient to break either frictional bond, members 70 and 72 of clip 66 will serve to retain hub 11 as they abut surface 19 thereof and members 84 and 86 will serve to retain male connector 32 as they abut the bulb 40 thereof.

The spacing of the clips on platform 50 is chosen such that the parts of the coupled components to be held may be engaged by the clips. It will be appreciated that it is also possible to space the clips such that they engage catheter tube 21 and tube 47 thus to prevent separation of the hub 11 and connector 32. It will be further appreciated that, in general, any pair of fluid conduits (e.g. tubing, valves, filters and the like) of an intravenous or intra-arterial access system in coupled relation may be retained securely in said coupled relation through the use of a device in accordance with the invention.

Various modifications may be made within the scope of the invention. For example, in place of one of clips 66, 68, 102 or 104, a connecting member may be formed integrally at one end with one of hub 11 or connector 32, while a clip either of the type shown in FIGS. 2–4 or FIGS. 5–7 is formed integrally at a second end thereof. Accordingly, when the other of hub 11 or connector 32 is coupled with the former, the clip may be engaged to secure the coupling against separation.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

I claim:

1. An apparatus for conveying vascular fluids to or from a patient, comprising:
    a tubular catheter having a frictional coupling;
    a tubular conduit for conveying vascular fluids to or from the catheter and having a coupling frictionally engaged with the frictional coupling of the catheter; and
    an apparatus for restraining disengagement of the frictional coupling between the catheter and tubular conduit, comprising:
    a base member;
    a clamp means affixed to one of the tubular catheter and conduit, comprising first and second members projecting from the base member and having opposed, diverging surfaces wedging said one of the tubular catheter and conduit radially therebetween;
    retaining means on the diverging surfaces of the clamp means for opposing disengagement of said one of the catheter and conduit from wedged relation between the surfaces of the first and second members;

whereby tubular catheters and conduits of various radial dimensions may be retained by the clamp means; and an affixing means spaced axially from the clamp means on the base member and affixed to the other one of the tubular catheter and conduit.

2. The apparatus of claim 1, wherein the retaining means comprises a plurality of axial ribs arranged in radially spaced relation on each of the opposed surfaces of the first and second members of the clamp means.

3. The apparatus of claim 1, wherein the affixing means comprises third and fourth members projecting from the base member and having opposed, uniformly diverging surfaces wedging said other one of the tubular catheter and conduit radially therebetween, and a second retaining means for opposing disengagement of said other one of the catheter and conduit from wedged relation between the surfaces of the third and fourth members.

4. The apparatus of claim 1, wherein the first and second members are radially spaced apart at the base member.

5. The apparatus of claim 1, wherein said one of the tubular catheter and conduit include a radially extending surface and the clamp means comprises an abutting means on the projecting members for abutting said radially extending surface to oppose an axial displacement of said one of the tubular catheter and conduit from coupled relation with the other one of the tubular catheter and conduit.

6. The apparatus of claim 1, wherein the affixing means comprises a connecting member formed integrally with said other one of the tubular catheter and conduit.

7. An apparatus for preventing separation of frictionally coupled tubular conduits in a vascular fluid access system, comprising:

a base member;

a first conduit clamp means for securely affixing to a first one of said tubular conduits, comprising first and second members projecting from the base member and having opposed, diverging surfaces for wedging said first tubular conduit radially therebetween;

first retaining means on the diverging surfaces of the first clamp means for opposing disengagement of said first tubular conduit from wedged relation between the opposed surfaces of the first and second members;

a second conduit clamp means for securely affixing to a second one of said tubular conduits, comprising third and fourth members projecting from the base member in axially spaced relation from the first conduit clamp means and having opposed, uniformly diverging surfaces for wedging the second tubular conduit radially therebetween; and second retaining means on the diverging surfaces of the second clamp means for opposing disengagement of the second tubular conduit from wedged relation between the opposed surfaces of the third and fourth members;

whereby tubular conduits of various radial dimensions may be retained by said first and second conduit clamp means.

8. The apparatus of claim 7, wherein the first and second retaining means comprise a plurality of axial ribs arranged in radially spaced relation on each of the opposed surfaces of the first and second conduit clamp means.

9. The apparatus of claim 7, wherein the first and second members are radially spaced apart at the base member and the third and fourth members are radially spaced apart at the base member.

10. The apparatus of claim 7, wherein the first and second conduit clamp means comprise respective abutting means on the projecting members for abutting radially extending surfaces of said first and second tubular conduits, respectively, to oppose an axial displacement of said first and second tubular conduits from coupled relation.

* * * * *